United States Patent [19]
Bogdanov

[11] 3,988,440
[45] Oct. 26, 1976

[54] REMEDY FOR TREATING GASTRITIS, GASTRIC AND DUODENAL ULCERS

[75] Inventor: Ivan Georgiev Bogdanov, Sofia, Bulgaria

[73] Assignee: DSO "Pharmachim", Sofia, Bulgaria

[22] Filed: Oct. 10, 1974

[21] Appl. No.: 513,845

[30] Foreign Application Priority Data
Oct. 11, 1973 Bulgaria .................................. 24712

[52] U.S. Cl. .............................. 424/115; 424/177; 424/195; 195/28 N; 195/96
[51] Int. Cl.$^2$ .................. A61K 35/74; A61K 37/02
[58] Field of Search .................. 424/195, 115, 177; 195/28 N, 96

[56] References Cited
UNITED STATES PATENTS
3,762,998  10/1973  Bogdanov ......................... 195/28 N Primary Examiner—Donald B. Moyer
Attorney, Agent, or Firm—Armstrong, Nikaido & Wegner

[57] ABSTRACT

A preparation is disclosed for treating gastritis and gastric and duodenal ulcers which comprises dried soya medium, sucrose, and dried *Lactobacillus bulgaricus* culture which has been obtained by cultivating the culture in a soya medium under anaerobic conditions at a temperature of between 35°–42° C, followed by spray drying the culture at a temperature of 150°–190° C. The culture consists of 25–35% protein, 45–52% sucrose, and 4–5.5% lactic acid.

1 Claim, No Drawings

REMEDY FOR TREATING GASTRITIS, GASTRIC AND DUODENAL ULCERS

This invention relates to a remedy for treating gastritis, gastric and duodenal ulcers and a method for obtaining same on the basis of *Lactobacilus bulgaricus*.

Ulcer in the stomach is known to be a polyetiological disease influenced both by locally active factors and functional disturbances in the vegetative and the central nervous system. Therefore the treatment of ulcer involves a great number of remedies affecting primarily the separate symptoms of the disease. The compositions most frequently used in these remedies are substances neutralizing the hydrochloric acid of the gastric juice. The temporary relief caused by the alkalizing remedies is followed by a reflex action intensifying the secretion of hydrochloric acid. In cases when permanent neutralization effect is obtained or even alkalization of gastric juice, disturbances in the digestion occur, which is normal at pH=2 — optimal for the action of pepsin.

In some therapeutic preparation along with the alkalizing ingredients there are also locally anesthetizing drugs and analgetic spasmolitic drugs which affect the other symptoms of the disease: pain nausea, vomiting.

It is a purpose of the present invention to provide a purely biological preparation that does not contain alkalizing, anesthetizing, spasmolitic and analgetic drugs; a preparation that has not only symptomatic but also therapeutic effect on the ulcer.

The advantages of the preparation are in its composition which contains absolutely harmless biological ingredients: soya, sugar and *Lactobacilus bulgaricus*. One pill of 2,5g contains 1.575g dried soya medium, dried bacterial bodies of Lactobacilus Bulgaricus and all biologically active products of its life-activity and 0,925g sugar. The biochemical composition of the preparation consists of 25–35% proteins, 45–52% sucroses, neutralization equivalent 1600–2100U, lactic acid 4–5,5%.

The presence of the specific *Lactobacilus bulgaricus* and the above biochemical composition, both characteristically stained after Gramm's and Neisser's method are reliable means for identifying the preparation.

Although the preparation does not contain alcalizing substances it quickly takes effect upon the uncomfortable feeling of pyrosis caused by the heightened activity of the gastric juice, due to the buffering effect of the proteins the preparation contains.

The preparation relieves the pain very soon though it does not contain analgetic, spasmolitic or locally anesthetizing drugs. The preparation has not only symptomatic effect against the various expressions of ulcers, but also causes and cures the ulcer process. One of the major advantages of the preparation is that it has curative effect on patients that have been treated with other remedies but with no success.

The therapeutic qualities of the preparation were tested on 360 patents in a number of hospitals: Clinic for Gastroenterology of ISUL Clinic for Internal Diseases of VVMI, the gastroenterologic sector of a city hospital in Sofia, the regional hospitals in the town of Kurrdjali, the town of Blagoevgrad and the town of Botevgrad. The main part of these patients (323) were under ambulatory treatment without giving up their work or daily routine, which means that the effect of the treatment is entirely due to preparation and to no hospitalization or special diet.

Out of all 360 patients 238 (66%) were suffering from ulcer of the duodenum, 93 (26%) had gastritis and 29 (3%) had gastric ulcer. Most of the patients were chronically ill, having been several times to hospitals and whose diagnosis has been defined as a result of numerous clinical and paraclinical examinations.

Only 43 (12%) of the patients had been suffering for 1 year. All the rest had been ill for 5, 10 and more years. During that time the patients had used with no effect a number of remedies or combinations of remedies: 64% of them had been taking Almagel; 35%—Mutesa; 35%—Spasmalgon; 31%—Neutracid, [31%—Vicalin; 17%—Calcium-Bromide-Atropine; 14%—Intiacid; 18%—Alumoxid and 12%—Oxiferroscarbon.

Of all 158 patients whose chief complaint was brashes and pyrosis in the stomach 54 felt relieved (34%) 5 minutes after taking the remedy, with 66 (42%) patients these symptoms disappeared in 10 minutes. Only 19 (12%) patients took more than 15 minutes to feel relieved. Of all 177 patients whose chief complaint was pain, 58 (33%) didn't feel it any more in the first 5 min. after taking the remedy. With 62 (35%) patients the pain disappeared in 10 min. and only 18 (10%) patients took more than 15 min. to feel relieved.

Of all 360 patients, regularly and systematically treated with the preparation, 198 (55%) had no more complaints by the 5th day, 101 by the 10th day and only 19 (5,2%) patients had no complaints after the 15th day. Three patients (0.8%) were not influenced by the preparation.

The remedy disagreed with no patient, even those supersensitive to a wide variety of antigens.

With 48 patients the curative effect was confirmed not only by the absence of complaints and passing from a strict diet to general food, but also radiographically by diminishing and even disappearing of the niches.

The method for obtaining the preparation consists in cultivating a specially selected strain of Lactobacilus Bulgaricus LB-51 (deposed under N.B51-1m/65) microbial cultures collection in the State Institute for control on medical remedies) in medium obtained from soya in anaerobic conditions and 35°–42° C temperature, following by drying the culture, adding of sugar, granulating of the mixture obtained and making pills.

EXAMPLE 1

In a fermentator of 2000 liter volume 60 kg soya groats are put and then 1500 l running water is poured over. The mixture is left to extract for 1 hour at 120° C. After cooling down to 70°–80° C the mixture undergoes centrofuging and 1% sucroses is added to the purified extract. Into a fermentator A of 200l volume 120l of this extract are poured and the rest is poured into a fermentator B of 2000l volume. The medium is sterilized for 45 min at 115° C. After cooling down to 40° C 6l pure culture *Lactobacilus bulgaricus*, cultivated in retorts with soya broth as described above, is sown into fermentator A. After 18 hour cultivating at 37° without stirring or aerating the culture from fermentator A in a sterile way is transplanted into the sterile medium in fermentator B. After 24 hour cultivating under the above mentioned conditions the culture in fermentator B is put to spray dry at 150° C "entrance" temperature and 75° C "exit" temperatures. 33 kg brownish dust with a specific sour taste of dry fruits is obtained. To the dry substance 19.8kg sucroses is added and it undergoes granulation without any other additional substances as it is common when granulating medical preparations. Afterwards the preparations is used either in the shape of granules or in the form of pills, obtained after pressing the above granule mass.

EXAMPLE 2

In a fermentator A, of 200 volume the medium is prepared consisting of 150l running water and 6 kg finely growed soya flour, whereafter 4% soya suspense is obtained. The medium is sterilized at 110° C for 45 min. under constant stirring. After cooling the medium down to 40° C, 6l pure culture from *Lactobacilus bulgaricus* in "soya broth" medium is inoculated into the fermentator. The "soya broth" is prepared as described in example 1. After 24 hour of cultivation at 37° C in anaerobic conditions the culture from fermentator A is transplanted (sterility observed into fermentator B of 2000l volume, which fermentator contains 1500l 4% soya suspention, prepared, sterilized and cooled down to 40° C as described for fermentator A of this example. After 24 hour of cultivation at 37° C without stirring or airing the culture from fermentator B undergoes spray drying under conditions described in example 1. 41kg dry substance is obtained, to which 24 kg sucrosis is added and the mixture is ready for granulating for making pills.

EXAMPLE 3

20l water is poured on 8 kg dry soya beans and left at indoors temperatures for 2 hours, Then, the soya beans are well washed with water until all external particles and dirt are completely removed. The soya beans thus washed are then minced in a meat-mincing machine, whereafter 150l water is poured on the mass obtained. After careful stirring the suspention it is emulsified by means of a coloidal mill, then it is filtered through four sheets of gauze in order to remove integuments and bigger particles and is then poured into a fermentator of 200l volume. The stable suspension thus obtained (soya milk) is sterilized at 110° C for 45min, then is cooled down to 40° C and 6l pure culture of *Lactobacilus bulgaricus* is inoculated on it, in soya broth, prepared as in example 1.

After 24 hours cultivation at 37° C without stirring or aeration the culture is spray dried at the temperatures described in example 1. 5,8 kg dry substance is obtained which is then mixed with 3.5kg sucrosis and granulated or made into pills.

What I claim is:

1. A preparation for treating gastritis, and gastric and duodenal ulcers which comprises dried soya medium, sucrose and dried Lactobacillus Bulgaricus culture (ATCC NO. 21815) which is obtained by cultivating said culture in soya medium under anaerobic conditions at a temperature between 35° to 42° C followed by spray drying said culture in a spray dryer at an entrance temperature of 150°–190° C and an exit temperature of 70°–85° C, said preparation having a chemical composition consisting of 25–35% protein, 45–52% sucrose, and 4–5.5% lactic acid.

* * * * *